United States Patent [19]

Iceland et al.

[11] Patent Number: 5,055,648

[45] Date of Patent: Oct. 8, 1991

[54] APPARATUS AND METHOD FOR MECHANICAL PROPERTIES TESTING

[75] Inventors: William F. Iceland, Los Alamitos; Robert J. Demonet, Westminster; Richard M. Jimenez, Chino; Donald W. Houston, Huntington Beach, all of Calif.

[73] Assignee: Rockwell International Corporation, El Segundo, Calif.

[21] Appl. No.: 457,591

[22] Filed: Dec. 27, 1989

[51] Int. Cl.$^5$ ................... H05B 6/06; H05B 6/10; G01N 3/18

[52] U.S. Cl. .................. 219/10.77; 219/10.41; 219/10.47; 219/10.57; 374/50; 374/56

[58] Field of Search .......... 219/10.41, 10.47, 10.57, 219/10.75, 10.77; 374/50, 45, 46, 56, 57, 126

[56] References Cited

U.S. PATENT DOCUMENTS

| | | | |
|---|---|---|---|
| 2,426,985 | 9/1947 | Darmara | 219/10.47 |
| 2,629,805 | 2/1953 | Body | 219/10.47 |
| 3,100,253 | 8/1963 | O'Connor | 219/10.47 |
| 3,611,787 | 10/1971 | D'Annessa et al. | 374/50 |
| 4,190,053 | 2/1980 | Sterzer | 374/112 |
| 4,580,449 | 4/1986 | Hatono et al. | 374/54 |
| 4,611,930 | 9/1986 | Stein | 374/126 |
| 4,618,267 | 10/1986 | Burke et al. | 374/50 |
| 4,812,052 | 3/1989 | Adam et al. | 374/50 |

FOREIGN PATENT DOCUMENTS 675632  8/1979  U.S.S.R. .................. 219/10.47

Primary Examiner—Philip H. Leung
Attorney, Agent, or Firm—Lawrence N. Ginsberg; Charles T. Silberberg

[57] ABSTRACT

An apparatus and method are described for maintaining a constant temperature across an electrically conductive specimen required to be mechanically tested. The invention includes resistance heating the specimen to a desired level during mechanical testing. The specimen is also simultaneously induction heated to a desired level. The resistance heating and inductive heating cooperate so as to heat the specimen to a desired substantially constant temperature during mechanical testing.

13 Claims, 4 Drawing Sheets

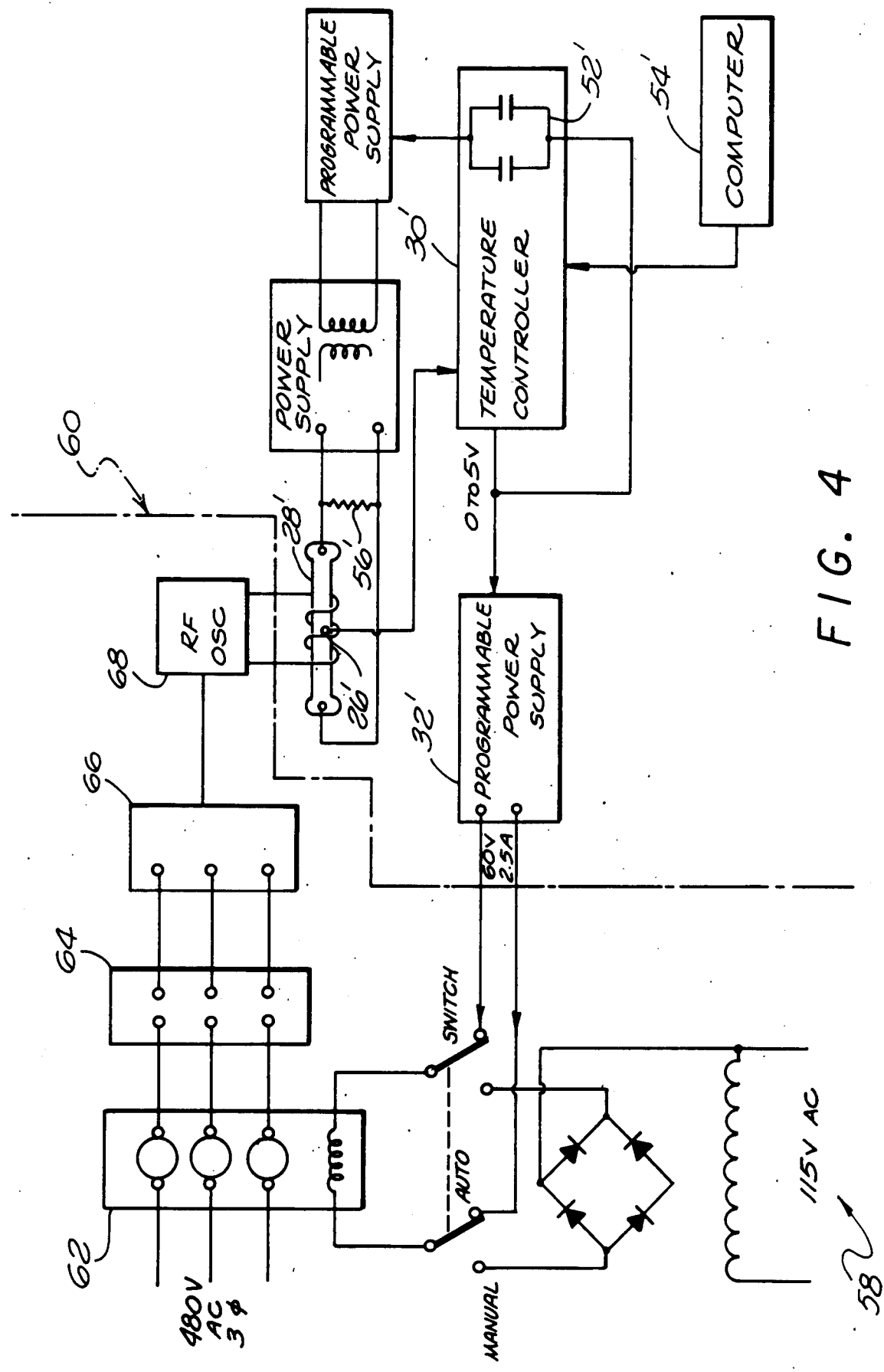

APPARATUS AND METHOD FOR MECHANICAL PROPERTIES TESTING

BACKGROUND OF THE INVENTION

1. Field of the Invention

This invention relates to apparatus and methods for mechanical properties testing and more particularly relates to an apparatus and method for maintaining a constant temperature across an electrically conductive specimen required to be mechanically tested.

2. Description of the Related Art

The development of new materials, for example in the aircraft industry, often requires the mechanical testing of large quantities of specimens at elevated temperatures. The enhancement of laboratory capabilities for more efficient testing of materials is imperative for progress in materials development.

Mechanical properties testing, including the testing for properties such as compression, tension and fatigue should be accomplished at a constant temperature within a defined gage length of the specimen. This testing establishes material characteristics such as ultimate tensile strength, yield strength and tensile elongation.

Traditionally, ovens and furnaces have been used for heating specimens for mechanical properties testing. Although these units perform satisfactorily, they have limited ability to reach the desired temperature within a short time. As a result of the size of the oven and the type of heating controls used up to several hours may elapse before elevated stable temperatures are realized. With several thousand specimens to be tested, this becomes a time consuming approach, resulting in an unacceptable cost.

Other methods for obtaining the desired temperature for mechanical properties testing have included the use of inductive heating sources. For example, U.S. Pat. No. 4,812,052, entitled "Apparatus For Creep Endurance Testing Structural Components", issued to Adam, et al, discloses use of induction heating for testing purposes. Similarly, U.S. Pat. No. 4,618,267, entitled "Remote Temperature-Set-Point Controller", issued to Burke, et al, discloses another device for carrying out mechanical strain tests using induction heating.

Use of induction heating produces a temperature drop during specimen elongation and, depending on the type of equipment used, requires relatively high power (i.e., approximately 2000 watts). Furthermore, use of induction heating requires a special coil design to obtain a constant temperature over a wide gage length (i.e. approximately two inches). In these cases, the coil windings must be specially spaced.

Still other methods for obtaining the desired temperature for mechanical properties testing have included the use of resistive heating sources. For example, U.S. Pat. No. 2,685,195, entitled "Fatigue Testing Machine", issued to L. A. Streblow, discloses a testing machine which uses resistive heating for testing purposes. Use of such resistive heating techniques, such as that disclosed in the Streblow reference, is generally undesirable because when the specimen is fractured, a larger arc results which is unsafe. Furthermore, undesirable hot spots develop.

U.S. Pat. No. 3,100,253, entitled "Temperature Control System for Specimen Testing", issued to W. J. O'Connor resolved one aspect of the problem with resistance heating techniques by utilization of a dummy load for arc suppression. However, even with arc suppression resistive heating techniques are deficient because arc suppression requires the interruption of the primary and secondary circuits of the transformer. This cannot be accomplished without temperature control penalties.

Therefore, it is a principle object of the present invention to provide a reliable, efficient method and apparatus for maintaining a constant temperature across a specimen being mechanically tested.

Another object of the present invention is to provide closed loop temperature control.

SUMMARY OF THE INVENTION

These and other objects are achieved by the present invention which is an apparatus and method for maintaining a constant temperature across an electrically conductive specimen required to be mechanically tested. The invention includes resistance heating means in electrical contact with the specimen for providing resistance heating of the specimen to a desired level during mechanical testing. Induction heating means is also included for providing simultaneous induction heating of the specimen to a desired level. The resistance heating and inductive heating cooperate so as to heat the specimen to a desired substantially constant temperature during mechanical testing.

With induction heating promoting a temperature drop during specimen elongation and resistance heating promoting a temperature rise, a self compensating constant temperature is produced.

In its more narrower aspects, the present invention includes closed loop temperature control systems for both resistance and induction heating. Furthermore, a novel non-contact temperature sensing means may optionally be provided which uses an emissive coating applied to the surface of the specimen and infrared detecting means.

Other objects, advantages and novel features of the present invention will become apparent from the following detailed description of the invention when considered in conjunction with the accompanying drawings.

BRIEF DESCRIPTION OF THE DRAWINGS

FIG. 4 is another preferred embodiment of the present invention using closed loop control for induction heating with resistance push through high-low temperature deviation relays.

The same elements or parts throughout the figures are designated by the same reference characters, while equivalent elements bear a prime designation.

DETAILED DESCRIPTION OF THE PREFERRED EMBODIMENTS

Figure 1:
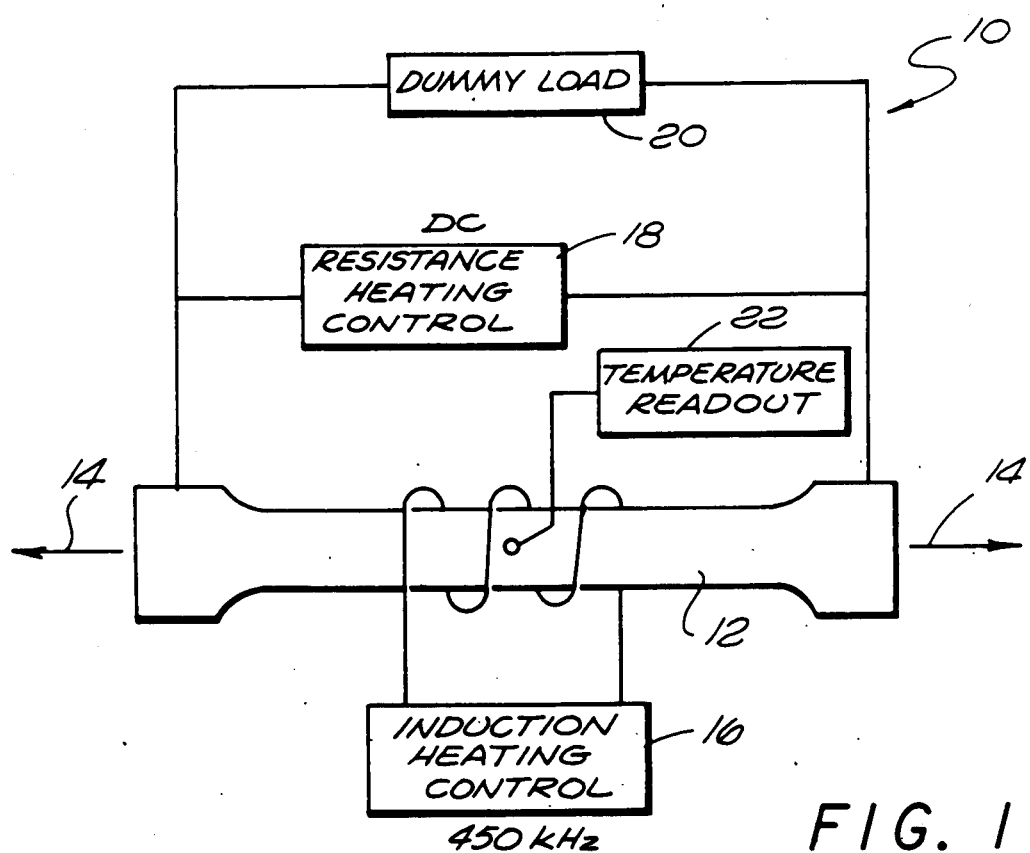
FIG. 1 is a simplified schematic illustration of the present invention.

Referring now to the drawings and the characters of reference marked thereon, FIG. 1 illustrates a simplified system set up of the present invention, designated generally as 10. An electrically conductive specimen 12 is utilized. The specimen 12 may be placed under tension, as shown by arrows 14, or otherwise tested for compression, fatigue or other mechanical properties. Thus, it is understood that in view of the broad utility of the present invention although application of the present invention will be described in detail with respect to tensile testing, such a description is for the purposes of illustration and not limitation.

Induction heating means 16 is provided for heating the specimen to a desired level during mechanical testing. Resistance heating means 18 is also provided for resistance heating of the specimen to a desired level during such a mechanical testing. Resistance heating means 18 may include, for example, a thermocouple in contact with the specimen 12.

With resistance heating, undesirable hot spots are created because, during a tensile elongation, the specimen cross-sectional area is reduced. However, during induction heating, a temperature drop is produced during specimen elongation. Thus, by combining the two effects, a self compensating system is realized. Coupling resistance heating with induction heating provides heretofore unrealized temperature regulation capabilities. Use of a dummy load 20 minimizes the undesired arcing condition experienced during specimen fracture.

To confirm the advantages of the present invention, the present inventors performed temperature deviation experiments. The objective was to minimize the specimen elongation temperature deviation experienced by using either induction or resistance heating, individually.

Figure 2:
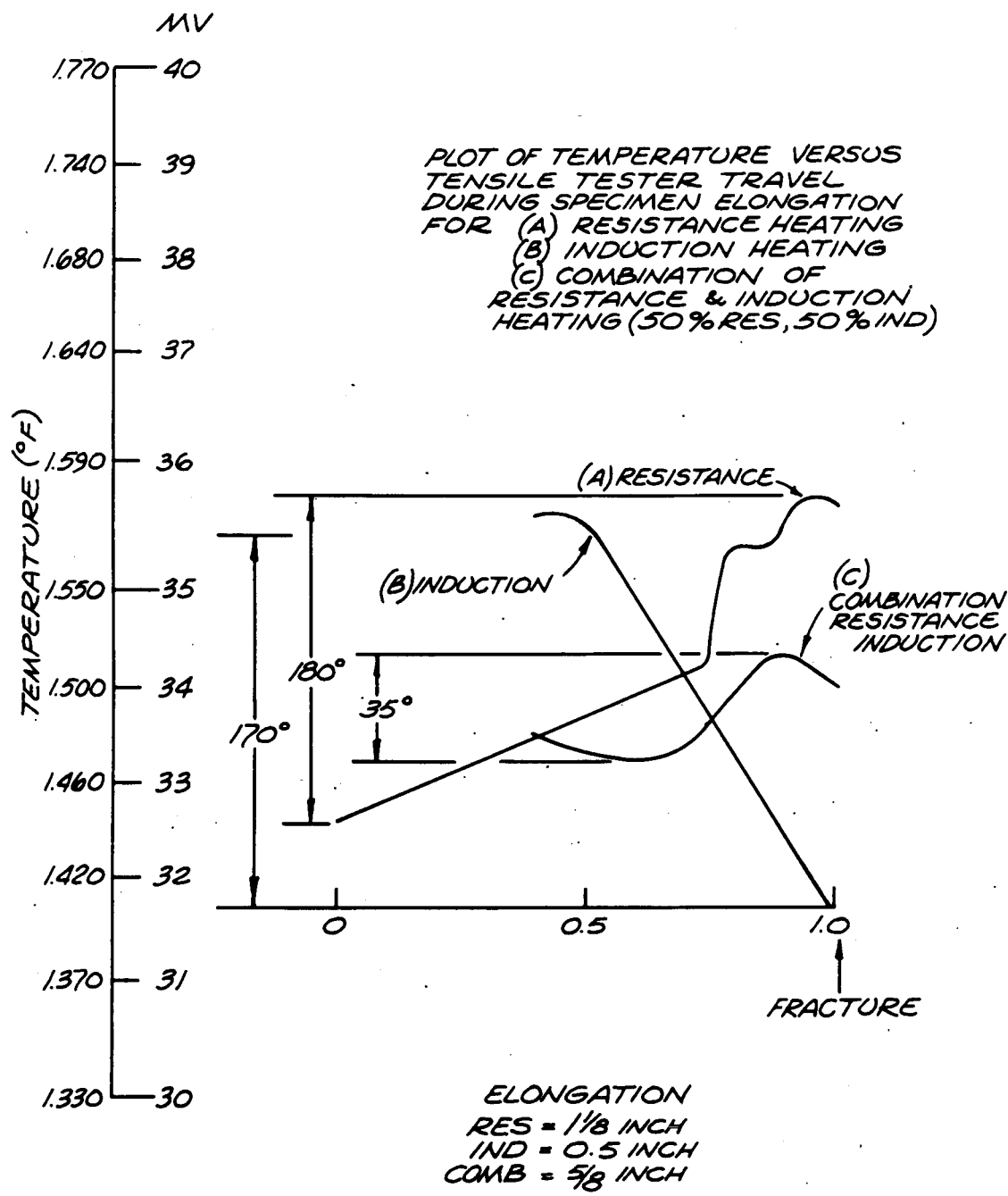
FIG. 2 is a plot of temperature versus tensile tester travel during specimen elongation for resistance heating, induction heating, and a combination of resistance and induction heating.

A number of 8-inch-long by 0.5-inch-wide by 0.060-inch-thick titanium 6 AL-4 V test specimens were fabricated and cleaned. A Type K thermocouple for temperature readout was spot welded on each specimen. The first test employed only resistance heating during specimen elongation. A Miller Electric power supply (constant current) powered the test specimen through a control cabinet. The specimen was heated to 1,500° F. by flowing current through the specimen. Curve A, shown in FIG. 2, was generated and illustrates rising temperature elongation characteristics.

A second test employed only induction heating. A Toccotron 450/kHz induction heating unit powered the test specimen through a 5-turn induction coil. The second specimen, when heated to 1,500° F., generated curve B shown in FIG. 2, during elongation. This curve displays a decreasing temperature characteristic.

A third test used the combination of resistance and induction heating. In this third test the specimen was powered to a nominal temperature of 1,500° F. using 50% resistance heating and 50% induction heating. Curve C was thus generated illustrating the system capability of decreasing the temperature deviation by a factor of 5. These tests demonstrated the viability of using resistance and induction heating, in combination, as a self-compensating temperature control. The present invention provides heating within a defined gage length. The induction coil winding densities at different positions over the gage length may be adapted to the desired levels to provide even heating across the specimen.

Although manual specimen temperature control means were used in the above examples, the advantages of the present invention can be optimized by utilizing an automatic temperature control system. Automatic control reduces specimen exposure to over temperature conditions.

Figure 3:
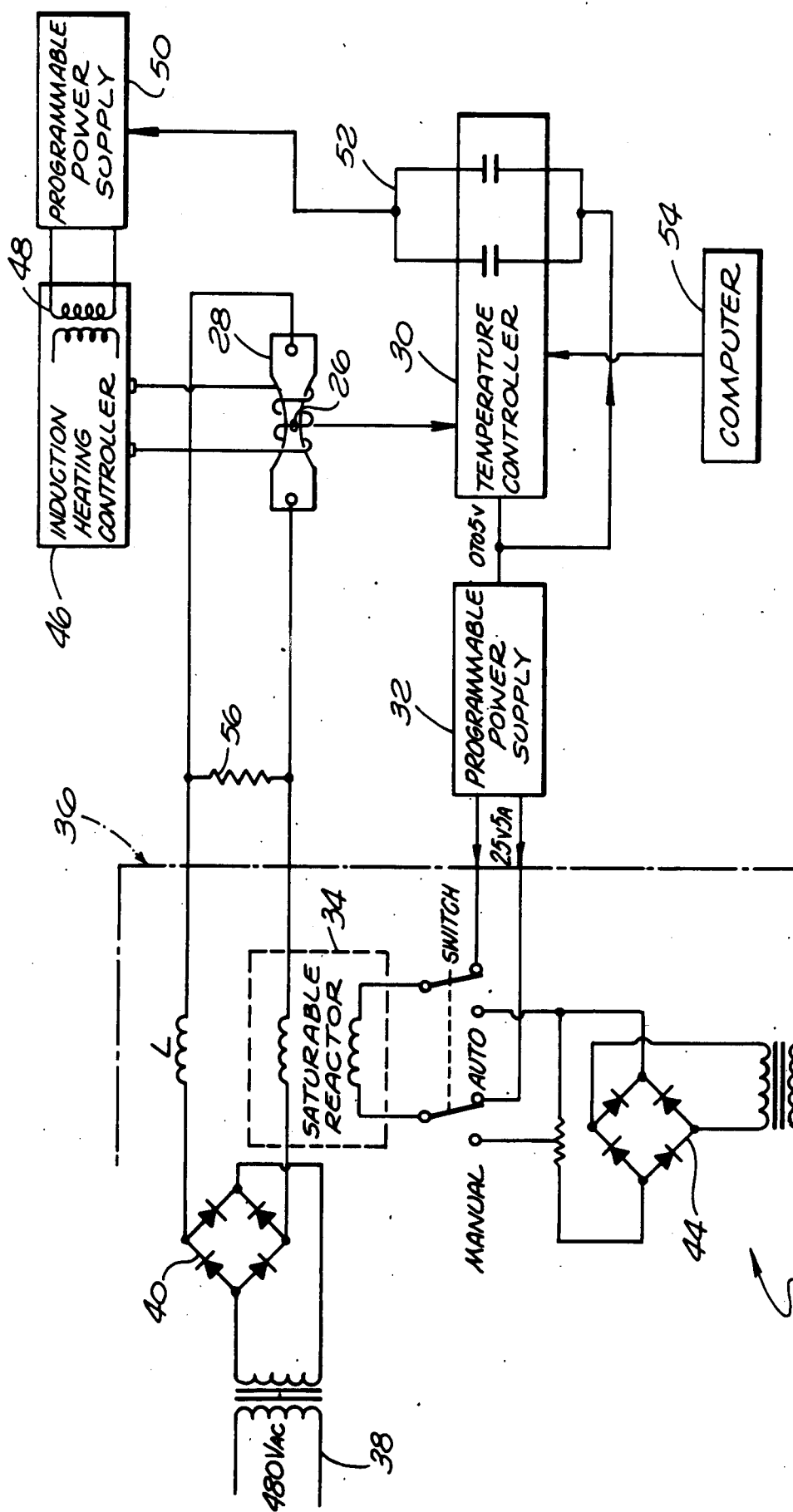
FIG. 3 is a preferred embodiment of the present invention using closed loop temperature control for resistance heating, with induction push through high-low temperature deviation relays.

Referring now to FIG. 3, a simplified diagram is shown for closed loop temperature control for resistance heating with induction push through high-low temperature deviation relays, this system designated generally as 24.

A thermocouple 26, such as a Type K thermocouple, is connected to the specimen 28 and provides input temperature information to a solid state temperature controller 30, such as that manufactured by Wahl Instruments, Inc.. The output of the temperature controller 30 is preferably between zero and 5 volts. The temperature controller 30 drives a programmable power supply 32. Programmable power supply 32 supplies the DC windings of a saturable reactor 34 of a resistance heating power supply represented within dashed lines 36. The programmable power supply 32 may be of the type manufactured by Electronic Measurements, Inc..

A DC winding controls the saturable reactor 34 to limit the current of the programmable power supply 36. The power supply 36 used may be of the type manufactured by Miller Supply Company, which requires 25 volts at 5 amps, for maximum power control.

For specimen heating, power is supplied through a 480 volt AC step-down transformer 38. A bridge rectifier 40 is provided to convert AC to DC and supply power to the specimen for resistance heating through inductor L.

If manual operation is desired, saturable reactor 34 is controlled by the potentiometer current control 42. Power is supplied through a 115 volt line through a bridge rectifier 44.

For induction heating, an induction heating controller 46 is utilized. The controller 46 may be, for example, a device distributed by Toccotron. The induction heating controller 46 includes a saturable reactor 48 with a DC winding. Another programmable power supply 50 supplies the DC winding of the saturable reactor 48.

High/low temperature deviation relays 52 are provided within the temperature controller 30. A deviation is slaved to the controlling set point and can be set at a plus or minus value above, equal to, or below the set point.

The temperature is preferably stabilized by proportional band, integral, and derivative (PID) electronic subsystems that are part of the temperature controller 30. A commercially available computer 54, for example one containing an IEEE 488 I/O board, permits automatic system control.

A dummy load 56 is maintained across the power supply 36 at all times during testing. Use of this dummy load 56 eliminates the undesired arcing condition by providing a power supply voltage output limit which is below the voltage required to sustain an arc. (For example, present Applicants have provided a dummy load with a resistive value sufficiently low to maintain a terminal voltage of the power supply at 3 volts. This level is well below the 7 to 50 volts required to sustain an arc.) The dummy load may, for example, be formed of a plurality of nickel cadmium strips.

Referring now to FIG. 4, a simplified diagram showing closed loop control for induction heating with resistance push through high-low temperature deviation relays is shown, designated generally as 58. In this embodiment, the resistive power supply and induction power supply have been interchanged to provide closed loop induction control. The induction power supply 60 includes a saturable reactor 62, a 3-phase high voltage transformer 64, a 3-phase rectifier 66 and an RF oscillator 68.

The choice between the FIG. 3 and FIG. 4 embodiments depends upon the specific application involved. Generally, if a large specimen is being tested, closed loop induction is preferred because of the relatively convenient heating abilities of induction coils. On the other hand, if a small specimen is used (i.e. compression testing), closed loop resistance is preferred because it is difficult to provide the sufficient induction coil windings.

For system testing a thermocouple may be used for providing temperature readings. However, present Applicants have developed a superior, non-contact temperature sensing system which is particularly adaptable for use with the principles of the present invention.

Figure 5:
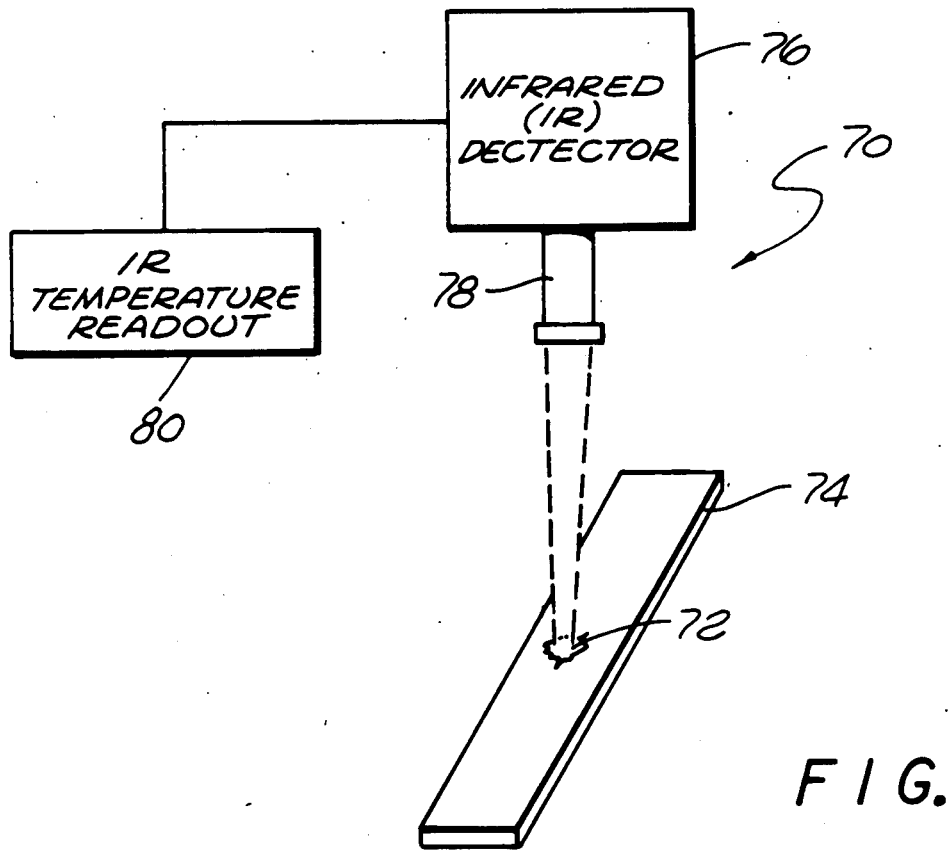
FIG. 5 is a schematic illustration showing use of an emissive coating for non-contact temperature sensing.

Referring now to FIG. 5, such a non-contact temperature sensing system is illustrated, designated generally as 70. An emissive coating 72 is applied to a small area on the surface of the test specimen 74. An infrared detector 76 with focussing optics 78 is used to measure the radiation emitted by the emissively coated surface. The IR detector 76 preferably operates at a wavelength greater than 2.4 microns. Temperature readings may be taken from readout device 80.

Use of this non-contact temperature sensing technique is particularly useful with the applications of the present invention because it minimizes any changes in the physical characteristics of the specimen which would otherwise result in erroneous test data. Use of thermocouples presents experimental obstacles because welding obviously affects the physical characteristics of the test specimen and is, therefore, unacceptable. Most presently available adhesive bonding sources are problematic at high temperatures.

During an experiment, present Applicants applied an emissive coating of AREMCO 620 onto a 0.5 square inch area of a titanium 6 AL-4 V test specimen. The brush-on coating was then cured in air—at 600° F. for a period of 20 minutes. A type K thermocouple used for temperature comparisons was resistance spot welded on the uncoated specimen side.

The heating of the coated test specimens was accomplished by induction heating. A 450 kHz–10 kW Toccotron induction unit generated sufficient power to elevate the coated specimens to temperatures in excess of 2,000° F. through a 5 turn-induction heating coil. The spacing selected between coil windings was of sufficient distance to prevent the coils from obscuring the specimen surface field of view. This permitted the coated test specimen IR radiation to be measured by the IR radiometer detector without interference by any obstructing objects.

A Huggins Inc.. Model 3121 operating at a wavelength of 2.4 to 2.7 microns was used to measure the radiation emitted by the emissive-coated test specimen. The radiometer optical head contained a focusing collector lens, a light modulator, an infrared detector, amplifiers, and a nonparallax viewing sight. The focusing lens focused to a specimen diameter spot size of 0.1 inch collected the specimen surface IR radiation from an area equal to 0.0078 square inch.

The light modulator periodically chops the incoming infrared beam to produce a modulated radiant flux at the detector. The detector converts the modulated incident radiation to an alternating signal voltage which is amplified and reads directly as temperature on the indicating meter.

With a digital temperature readout connected to the thermocouple welded to the uncoated side of the test specimen (acting as a standard), a direct comparison between the IR radiation temperature and thermocouple temperature was measured.

Thermocouple and IR measurements made simultaneously at 1,200° F., 1,500° F., and 1,800° F. resulted in a temperature measurement variance of ±2 percent (the accuracy of the instrumentation).

Obviously, other modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. An apparatus for maintaining a constant temperature across an electrically conductive specimen required to be mechanically tested, including:
   (a) resistance heating means, in electrical contact with an electrically conductive specimen, for providing resistance heating of said specimen to a desired level during mechanical testing;
   (b) induction heating means for providing substantially simultaneous induction heating of said specimen to a desired level; and,
   (c) controller means, including a closed loop control system, for automatically providing cooperation between the resistance heating and inductive heating so as to heat the specimen to a desired substantially constant temperature during mechanical testing.

2. The apparatus of claim 1, wherein said resistance heating means and induction heating means include means for providing heating within a defined gage length.

3. The apparatus of claim 1, wherein said resistance heating means includes a parallel dummy load for dissipating the abrupt energy formation resulting from specimen fracture.

4. The apparatus of claim 1, wherein said controller means includes non-contact temperature sensing means for determining the temperature of said specimen while minimizing any changes in the physical characteristics of the specimen which could result in erroneous test data.

5. The apparatus of claim 4, wherein said non-contact temperature sensing means includes:
   (a) an emissive coating applied to an area on the surface of said specimen, said area being sufficiently small such that the physical characteristics of the test specimen which effect temperature readings are not substantially effected; and
   (b) infrared detecting means directable toward said emissive coating for providing indications of the specimen's temperature.

6. The apparatus of claim 1, wherein said controller means includes closed loop temperature control for resistance heating with induction push through high-low temperature deviation relays.

7. The apparatus of claim 1 wherein said controller means includes closed loop temperature control for induction heating with resistance push through high-low temperature deviation relays.

8. A method of maintaining a constant temperature across an electrically conductive specimen required to be mechanically tested, including:
   (a) resistance heating said specimen to a desired level during mechanical testing, and;
   (b) simultaneously induction heating said specimen to desired level; and,
   (c) employing a closed loop system for automatically controlling said resistance heating and inductive heating, said resistance heating and inductive heating cooperating so as to heat the specimen to a desired substantially constant temperature during mechanical testing.

9. The method of claim 8, wherein said resistance heating means and induction heating provide heating within a defined specimen gage length.

10. The method of claim 8, further including the step of providing a parallel dummy load for dissipating the abrupt energy formation resulting from specimen fracture.

11. The method of claim 8 wherein the step of automatically controlling said cooperation includes non-contacting temperature sensing, including:
   (a) applying an emissive coating to an area on the surface of said specimen, said area being sufficiently small such that the physical characteristics of the test specimen which effect temperature readings are not substantially effected; and
   (b) directing infrared detecting means toward said emissive coating for providing indications of the specimen's temperature.

12. The method of claim 8, wherein said step of automatically controlling includes closed loop temperature controlling for resistance heating with induction push through high-low temperature deviation relays.

13. The method of claim 8, wherein said step of automatically controlling includes closed loop temperature controlling for induction heating with resistance push through high-low temperature deviation relays.

* * * * *